(12) United States Patent
Sun et al.

(10) Patent No.: US 7,489,965 B2
(45) Date of Patent: Feb. 10, 2009

(54) APPARATUS FOR NEUROMUSCULAR MEASUREMENT AND CONTROL

(75) Inventors: Ying Sun, Wakefield, RI (US); Jiang Wu, Norwood, MA (US); Leon P. Collis, Plymouth, MA (US); Robert B. Hill, Kingston, RI (US)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 492 days.

(21) Appl. No.: 10/957,930

(22) Filed: Oct. 4, 2004

(65) Prior Publication Data

US 2005/0090865 A1    Apr. 28, 2005

Related U.S. Application Data

(63) Continuation of application No. PCT/US03/10317, filed on Apr. 4, 2003.

(60) Provisional application No. 60/369,964, filed on Apr. 4, 2002.

(51) Int. Cl.
    *A61N 1/00*    (2006.01)
(52) U.S. Cl. .......................................... 607/2
(58) Field of Classification Search ............... 607/1, 607/2, 3, 45, 46, 48–50, 53–57, 62
    See application file for complete search history.

(56) References Cited

U.S. PATENT DOCUMENTS

| 4,977,895 A | 12/1990 | Tannenbaum |
| 6,665,562 B2 * | 12/2003 | Gluckman et al. ............. 607/2 |

* cited by examiner

*Primary Examiner*—George R Evanisko
(74) *Attorney, Agent, or Firm*—Gauthier & Connors LLP

(57) ABSTRACT

A dynamically configurable clamping device for applying a desired electrical current to a tissue membrane includes an input lead electrically connected to the tissue membrane to provide a sensed signal indicative of voltage across the membrane. An input circuit includes an analog-to-digital converter, and is responsive to the sensed signal and provides a digitized signal indicative of the sensed signal. A digital signal processor executes selected program instructions to operate in a selected one of (i) a voltage clamp mode, (ii) a current clamp mode or (iii) a dynamic clamp mode based upon the state of a mode selection signal indicative of the selected operating mode. The digital signal processor provides a digital current command signal indicative of the current to be applied to the tissue membrane. An output circuit receives the digital current command signal, and generates a current signal indicative thereof. An output lead receives and applies the current signal to the tissue membrane. Digital feedback control is advantageous over the traditional systems by providing programmability, capability for dynamic changes of clamping modes, hardware simplification, and integration of multichannel clamping systems. The digital signal processor in the feedback loop provides programmability in the control algorithm.

13 Claims, 4 Drawing Sheets

APPARATUS FOR NEUROMUSCULAR MEASUREMENT AND CONTROL

PRIORITY DATA

This application is a continuation of International Patent Application No. PCT/US03/10317, filed Apr. 4, 2003, which claims the benefit of U.S. Provisional Application No. 60/369,964 filed Apr. 4, 2002, and hereby incorporated by reference.

BACKGROUND OF THE INVENTION

The present invention relates to the field of devices to study the electrophysiology of nerve and muscle tissues, and in particular to a dynamically configurable clamp device used to measure and control nerve and muscle tissues.

A neuroscience laboratory is generally equipped with at least one voltage clamp system to study the electrophysiology of nerve and muscle tissues. Current-voltage relations across excitable membranes are time varying, nonlinear, and spatially distributive. By clamping the membrane potential to a step function, the voltage clamp system momentarily achieves spatial coherence and voltage invariance. The current injected back into the cell for maintaining a constant membrane potential can be equated to the ionic current that induces an action potential. Further decomposition of the ionic current due to sodium, potassium, and calcium can be done by ionic substitutions in the bathing solution of the tissue.

Half a century ago Cole (Cole, K. S., *Dynamic electrical characteristics of the squid axon membrane*, Arch. Sci. Physiol. 3, 253-258) introduced the voltage clamp technique, which lead to the landmark study of axonal current-voltage relations by Hodgkin, Huxley, and Katz in 1952 (Hodgkin, A. L., and Huxley A. F., *Currents Carried by Sodium and Potassium Ions through the Membrane of the Giant Axon of Lologo*, J. Physiol. Lond. 116, 449-472, 1952; Hodgkin, A. L., and Huxley A. F., *A Quantitative Description of Membrane Current and its Application to Conduction and Excitation in the Nerve*, J. Physiol. Lond. 116, 500-544, 1952; Hodgkin, A. L., Huxley A. F. and Katz B., *Measurement of Current-Voltage Relations in the Membrane of the Giant Axon of Loligo*, J. Physiol. Lond. 116, 424-448, 1952). Hodgkin and Huxley were awarded the Nobel Prize for their contributions in neuroscience. The voltage clamp is arguably the most useful technique for studying membrane excitation to date.

The dynamic clamp developed by Robinson (Robinson, H. P., and Kawai, N., *Injection of Digitally Synthesized Synaptic Conductance Transients to Measure the Integrative Properties of Neurons*, J. Neurosci. Methods 49, 157-165, 1993; Robinson, H. P., *Conductance Injection-Letter to the Editor*, with Reply by Sharp, A. A., O'Neil M. B., Abbott, L. F., and Marder, E., Trends in Neurosci. 17, 147-148 1994) and Sharp et al. (Sharp, A. A., O'Neil, M. B., Abbott, L. F., and Marder E., *Dynamic Clamp: Computer-Generated Conductances in Real Neurons*, J. Neurophysiol. 69, 992-995, 1993; Sharp, A. A., O'Neil, M. B., Abbott, L. F., and Marder E., *The Dynamic Clamp: Artificial Conductances in Biological Neurons*. Trends in Neurosci. 16, 389-394, 1993) has been used to create an artificial synapse by measuring voltage in one neuron and injecting current into another neuron. Their instruments were based on the traditional voltage clamp-amplifier coupled with a PC data acquisition system. Such a system does not provide sufficient speed and flexibility to be a general instrument for neuroscience research.

Current clamps are also known. However, prior art voltage, current and dynamic clamps have been dedicated, non-configurable devices that perform only their respective voltage, current or dynamic clamp functions, respectively. That is, prior art voltage clamps would only operate as a voltage clamp, and could not be reconfigured to operate as a dynamic clamp, and visa versa.

Therefore, there is a need for a system that can automatically be configured to operate in a desired clamp mode in response to a user command.

SUMMARY OF THE INVENTION

Briefly, according to an aspect of the invention, a device for applying a desired electrical current to a tissue membrane includes an input lead electrically connected to the tissue membrane to provide a sensed signal indicative of voltage across the membrane. An input circuit includes an analog-to-digital converter, and is responsive to the sensed signal and provides a digitized signal indicative of the sensed signal. A digital signal processor executes selected program instructions to operate in a selected one of (i) a voltage clamp mode, (ii) a current clamp mode or (iii) a dynamic clamp mode based upon the state of a mode selection signal indicative of the selected operating mode. The digital signal processor provides a digital current command signal indicative of the current to be applied to the tissue membrane. An output circuit receives the digital current command signal, and generates a current signal indicative thereof. An output lead receives and applies the current signal to the tissue membrane.

In one embodiment, the dynamically configurable clamp device includes three functional units—an observer, a controller and a digital signal processor. The observer comprises a pre-amplifier and an analog-to-digital converter for measuring the membrane potential in a neuron or a muscle cell. A controller comprises a constant current source (CCS) driven by a digital-to-analog converter. A digital signal processor (DSP) closes a feedback loop, using the membrane potential to determine the current injected back into the cell. The digital control algorithm can be downloaded from a PC to the DSP and is implemented by the DSP in real time. The clamp unifies the design of the traditional analog systems for voltage clamp, current clamp and dynamic clamp.

Advantageously, digital feedback control provides programmability, capability for dynamic changes of clamping modes, hardware simplification, and integration of multi-channel clamping systems.

The digital signal processor in the feedback loop provides programmability in the control algorithm. The traditional voltage clamp, current clamp, and dynamic clamp have been accomplished by use of different, separate systems. The device of the present invention accomplishes all clamping needs in a single integrated system.

Multiple control algorithms can be stored in the digital signal processor. The control algorithms can be changed instantaneously on user command or triggered by specifically preprogrammed events.

The analog front-end of the system is significantly simplified. Instead of designing a closed-loop feedback system, the input voltage measurement and the output current injection are decoupled. Feedback control is left to the software implementation in the digital signal processor.

Research in the field of neuroscience has expanded from the study of a single neuron to multiple neurons and their inter-connection network. The dynamically configurable clamping device provides a programmable multi-channel system to study neuronal networks.

In one embodiment, the dynamically configurable clamping device is configured as a voltage clamp with a single electrode. This may be accomplished by time multiplexing voltage measurement and current injection on a single electrode.

The dynamically configurable clamping device may also be used for the control prosthetic limbs, brain-machine interface, treatments of neurological diseases and the development of artificial sensory systems such as artificial retina, artificial cochlear, and artificial nose.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
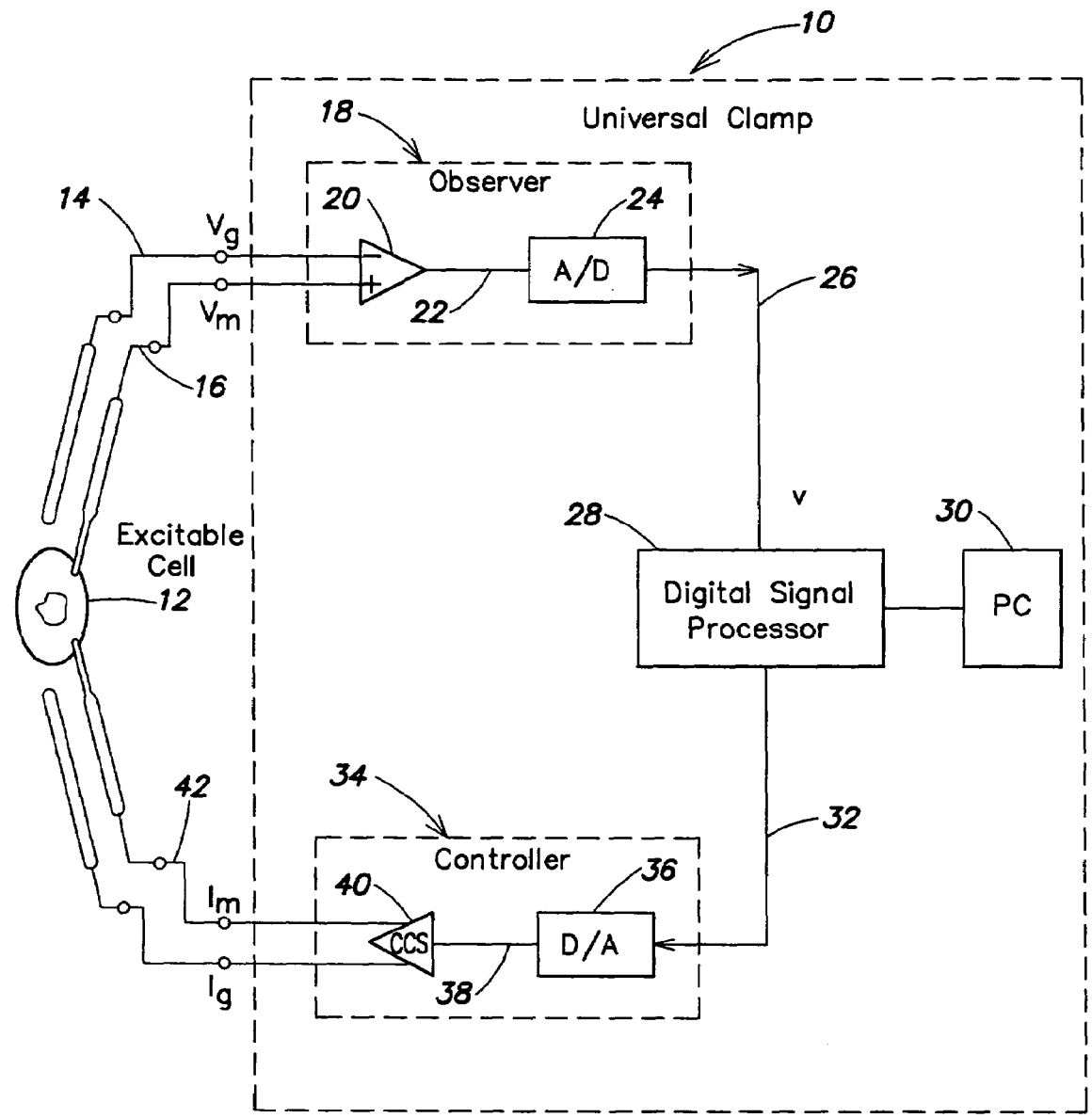
FIG. 1 is a functional block diagram illustration of a dynamically configurable clamping device.

FIG. 1 is a block diagram illustration of a dynamically configurable clamping device 10 that is operably connected to an excitable cell membrane 12. Leads 14, 16 provide a signal to an input circuit 18 that includes an input amplifier 20. Lead 14 is preferably connected to a reference voltage, such as ground, and the signal input to the input circuit 18 is preferably indicative of voltage. The input amplifier 20 provides a signal on a line 22 to an analog-to-digital converter (ADC) 24, and the resultant digitized signal is output on a line 26 to a digital signal processor (DSP) 28. The digitized signal on the line 26 is indicative of membrane voltage. Suitable DSP's include, for example, the TMS 320 C6000 series from Texas Instruments, the ASDP-21160 series and TigerSHARC series from Analog Devices.

The DSP 28 communicates with a mode selection device 30, such as for example a personal computer (PC). Executable DSP control routines can be downloaded from the PC 30 to the DSP 28, and executed by the DSP 28. The control routines executed by the DSP 28 process the digitized input signal on the line 26 and provide a current command output signal on a line 32 indicative of a electrical current to be applied to the cell 12. The output signal on the line 32 is input to output circuitry 34 that includes a digital-to-analog converter (DAC) 36. The DAC 36 provides an analog current command signal on a line 38 indicative of the current to be applied the cell 12. The output circuitry 34 also includes a current source 40, such as a constant source, responsive to the analog signal on the line 38, and provides a current signal on a line 42 to the cell 12. This current drives the cell to a desired potential. Significantly, this system utilizes discrete time closed loop control to provide a dynamically configurable clamp.

The control routine to be executed by the DSP is automatically selected based upon the user selected operating mode of the clamp 10. The selectable operating modes may include voltage clamp mode, current clamp mode and dynamic clamp mode. A voltage clamp halts the normal voltage excursions of a clamped neuron, and may employ pharmacological agents to isolate a single conductance. A current clamp injects current into a neuron to either depolarize or hyperpolarize a neuron. A dynamic clamp introduces artificial voltage and time-dependent conductances into biological neurons.

Since the DSP 28 executes a control routine that provides a closed loop control system, the control routines may support several known control system architectures such as proportional (P), proportional-integral (PI) and proportional-integral-derivative (PID). Advantageously, the system of the present invention provides digital feedback control and the ability to dynamically change the operating mode of the clamp. In contrast, prior art systems operated in a single unalterable mode.

Figure 2:
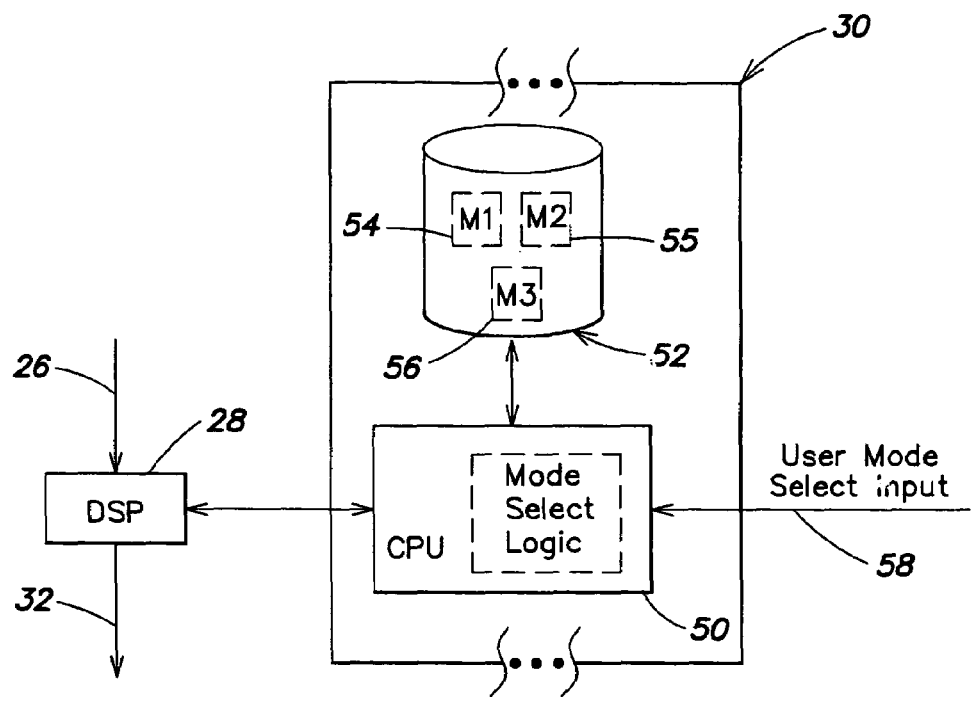
FIG. 2 is a functional block diagram illustration of a first embodiment of the configurable clamp of FIG. 1 wherein executable program instructions associated with the various operating modes of the user configurable clamp are selectively downloaded to the DSP in response to a mode selection signal.

FIG. 2 is a simplified functional block diagram illustration of a first embodiment of the user configurable clamp of FIG. 1, wherein executable program instructions associated with the various operating modes of the user configurable clamp are selectively downloaded to the DSP 28 in response to a mode selection. The PC 30 includes a CPU 50, and a memory device 52 that includes a plurality of DSP executable software routines 54-56. The PC 30 receives a clamp mode input signal on a line 58 from a user (e.g., a via a keyboard or other input device), and in response the CPU 50 selects the DSP executable software routine 54-56 associated with the mode specified by the clamp mode input signal on the line 58. For example, the DSP executable software routines 54-56 may be associated with the voltage clamp mode, the current clamp mode and the dynamic clamp mode, respectively. Once the selected routine 54-56 is downloaded to the DSP 28, the DSP begins operating in the selected mode by executing the downloaded routine.

Figure 3:
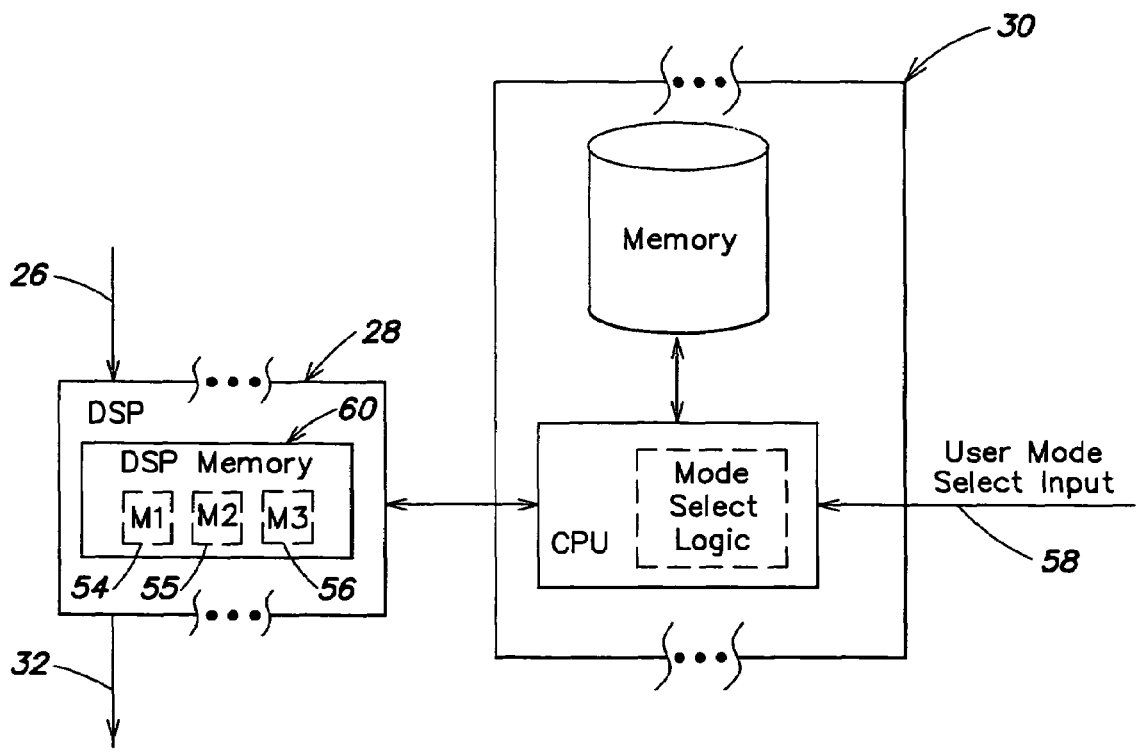
FIG. 3 is a functional block diagram illustration of a second embodiment of the configurable clamp of FIG. 1 wherein executable program instructions associated with the various operating modes of the user configurable clamp are stored in the DSP and selectively executed in response to a mode selection signal.

FIG. 3 is a functional block diagram illustration of a second embodiment of the user configurable clamp of FIG. 1, wherein executable program instructions associated with the various operating modes of the user configurable clamp are stored in the DSP 28 and selectively executed in response to a mode selection. In this embodiment, DSP memory 60 includes the various DSP executable software routines 54-56. The PC 30 receives the clamp mode select signal on the line 58 and provides a signal indicative thereof to the DSP 28, which then selects from the DSP executable software routine 54-56 for the executable routine associated with the selected mode. The DSP then begins operating in the selected mode by executing the downloaded routine.

Figure 4:
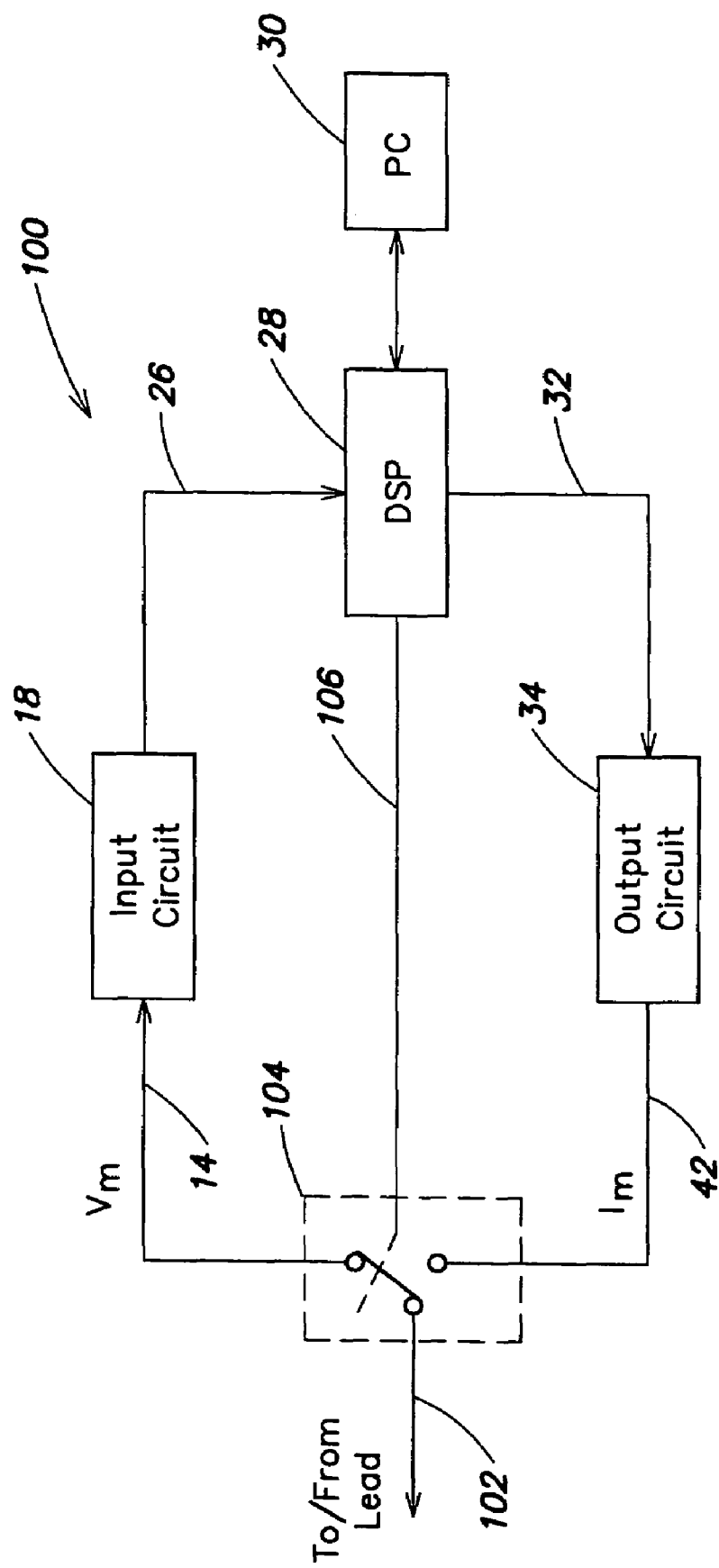
FIG. 4 is a functional block diagram illustration a user configurable clamp that includes a single lead connected to the tissue.

FIG. 4 is a functional block diagram illustration a user configurable clamp 100 that includes a single lead 102 connected to the tissue (not shown). This embodiment is substantially the same as the embodiment illustrated in FIG. 1, with the principal exception that only a single lead is required. The lead 102 is selectively coupled to either the input signal on the line 14, or the output signal on the line 42 by a switch 104 (e.g., a semiconductor switch). The switch 104 is controlled by a signal on a line 106 from the DSP 28.

Figure 5:
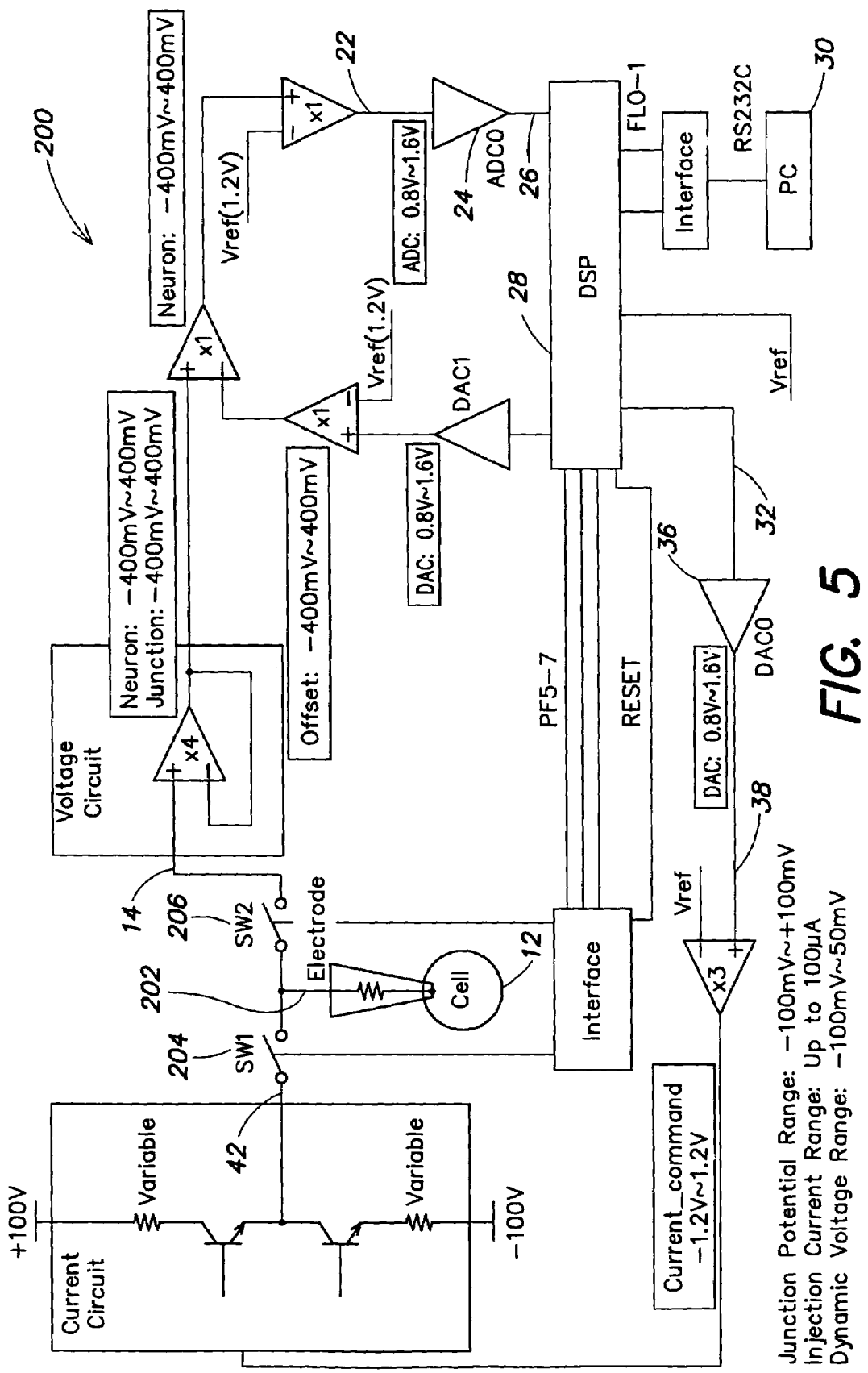
FIG. 5 is a functional block diagram illustration of a second user configurable clamp that includes a single lead connected to the tissue.

FIG. 5 is a functional block diagram illustration a second user configurable clamp 200 that includes a single lead 202 connected to the tissue. In this embodiment two switches 204, 206 are used to selectively couple the single lead to either the input signal on the line 14 or the output signal on the line 42.

Although embodiments of the present invention have been illustrated with the ADCs and DACs being outside the DSP, it is contemplated that these devices may be placed on a single integrated circuit. In addition, although the system has been discussed in the context of employing a DSP, any discrete time programmable device that executes program instructions may be used to perform the control function.

Although the present invention has been shown and described with a preferred embodiment thereof, various changes, omissions and additions to the form and detail thereof, may be made therein, without departing from the spirit and scope of the invention.

What is claimed is:

1. A device for applying a desired current to a tissue membrane, said device comprising:
    an input lead adapted to be electrically connected to the tissue membrane to provide a sensed signal indicative of voltage across the membrane;
    an input circuit that includes an analog-to-digital converter, and is responsive to said sensed signal and provides a digitized signal indicative of said sensed signal;
    a digital signal processor operable in a voltage clamp mode, a current clamp mode and a dynamic clamp mode, said processor executes selected program instructions to operate in a selected one of said (i) a voltage clamp mode, (ii) a current clamp mode or (iii) a dynamic clamp mode based upon the state of a mode selection signal indicative of the selected operating mode, wherein said digital signal processor provides a digital current command signal indicative of the current to be applied to the tissue membrane;
    an output circuit that receives said digital current command signal, and generates a current signal indicative thereof; and
    an output lead adapted to be electrically connected to the tissue membrane, which receives and applies said current signal to said tissue membrane.

2. The device of claim 1, comprising a mode selection device that provides said mode selection signal in response to a selection made by a user.

3. The device of claim 2, wherein said mode selection device is configured an arranged as a personal computer.

4. The device of claim 2, wherein said mode selection device comprises a central processing unit.

5. The device of claim 4, wherein said output circuit comprises a digital-to-analog converter that provides an analog current command signal to a current source that provides said current signal in response to said analog current command signal.

6. The device of claim 5, wherein said program instructions include control loop program instructions to provide a proportional-integral (PI) compensator.

7. The device of claim 5, wherein said program instructions include program instructions wherein said digital signal processor provides a proportional-integralderivative (PID) compensator.

8. A dynamically configurable clamping device for applying a desired current to a tissue membrane, said device comprising:
    a lead electrically adapted to be connected to the tissue membrane;
    an input circuit that is selectively coupled to said lead to receive a sensed signal indicative of the voltage across the membrane, wherein said input circuit includes an analog-to-digital converter that is responsive to said sensed signal and provides a digitized signal indicative of said sensed signal;
    a processor that executes operable in a voltage clamp mode, a current clamp mode and a dynamic clamp mode, said processor executes selected program instructions to operate in a selected one of said (i) a voltage clamp mode, (ii) a current clamp mode or (iii) a dynamic clamp mode based upon the state of a mode selection signal indicative of the selected operating mode, wherein said processor provides a digital current command signal indicative of the current to be applied to the tissue membrane;
    an output circuit that receives said digital current command signal, and generates a current signal indicative thereof; and
    a switch for selectively coupling a selected one of said current signal and said input circuit to said lead.

9. The device of claim 8, comprising a mode selection device that provides said mode selection signal in response to a selection made by a user.

10. The device of claim 9, wherein said mode selection device is configured an arranged as a personal computer.

11. The device of claim 9, wherein said mode selection device comprises a central processing unit.

12. The device of claim 8, wherein said program instructions include control loop program instructions to provide a proportional-integral (PI) compensator.

13. The device of claim 8, wherein said program instructions include program instructions wherein said processor provides a proportional-integral-derivative (PID) compensator.

\* \* \* \* \*

UNITED STATES PATENT AND TRADEMARK OFFICE
CERTIFICATE OF CORRECTION

PATENT NO.        : 7,489,965 B2                                     Page 1 of 1
APPLICATION NO.   : 10/957930
DATED             : February 10, 2009
INVENTOR(S)       : Ying Sun et al.

It is certified that error appears in the above-identified patent and that said Letters Patent is hereby corrected as shown below:

In the masthead, the inventor information should read as follows:

(75) Inventors: Ying Sun, West Warwick, RI (US); Jiang Wu, Norwood, MA (US); Leon B. Collis, Plymouth, MA (US); Robert B. Hill, Kingston, RI (US)

Signed and Sealed this

Twenty-first Day of April, 2009

JOHN DOLL
*Acting Director of the United States Patent and Trademark Office*